May 12, 1953 F. RAHBEK Plant Pat. 1,187
SAINTPAULIA PLANT
Filed April 23, 1951
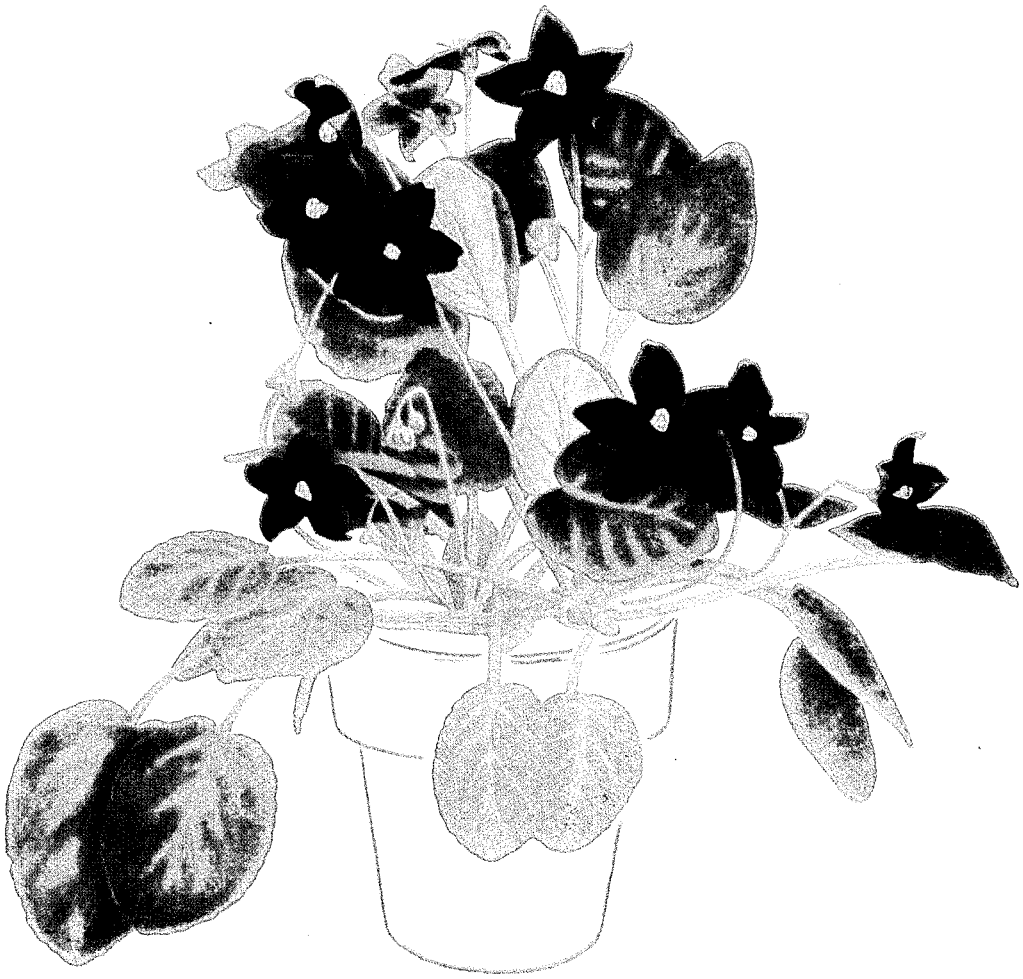
Inventor:
Frode Rahbek,
By Z. T. Wolcott Smith
Attorney.

Patented May 12, 1953

Plant Pat. 1,187

UNITED STATES PATENT OFFICE 1,187

SAINTPAULIA PLANT

Frode Rahbek, Primos, Pa., assignor to Robert Craig Company, Inc., Norwood, Pa., a corporation of Pennsylvania Application April 23, 1951, Serial No. 222,490

1 Claim. (Cl. 47—60)

The present discovery relates to a new and distinct variety of *Saintpaulia ionantha* grandiflora (Hort.) plant which originated as a sport of the well known unpatented Saintpaulia "Blue Boy" variety. This sport was discovered in the Saintpaulia section of commercial greenhouses at Norwood, Pennsylvania, which are under my supervision and control.

The asexual reproduction of this new variety of Saintpaulia has been accomplished by me at Norwood, Pennsylvania. The asexual reproduction of this new variety since May, 1948, has shown its qualities to be permanently fixed.

To propagate the plant, leaf cuttings are placed in prepared sand until rooted and until a crown develops. A good root system develops in three weeks. However, in the greenhouses at Norwood, Pennsylvania, these cuttings are left in the sand until a crown develops, a further period of five weeks, at which time the young plants are transplanted to 2¼-inch pots.

The novelty of the new variety resides in the entirely new shape of the bloom, the regular appearance of at least four and usually five stamens, in contrast to the two stamens usual in other varieties, and the large size of the bloom, averaging 1⅜ to 1¾ inches in diameter.

The accompanying illustration shows a potted plant of the new variety, with typical flowers and leaves.

In structure the new variety is similar to the "Blue Boy" variety. It is a stemless hairy perennial. The leaf is ovate, slightly serrate, and averages two inches in length by one and one-half inches in width. The upper side is a medium yellow-green color and hirsute. The under side is an off-while color and slightly hirsute texture. On the young leaf, the mid rib and veins are a reddish purple color matching the petiole. As the leaf matures, this reddish purple color fades to a dull off-while. The mature petiole is sturdy, oval at base, rounded at leaf end; $\frac{3}{16}$ to ¼ inch at basal end, and ⅛ to $\frac{3}{16}$ inches in diameter at leaf end. It is moderately hirsute, color red purple when immature, fading to pale green with slight purplish overtones in maturity.

The new variety has the free blooming habit of the "Blue Boy" variety. Fairly upright flowers are borne in red purple peduncled few flowered cymes. The flower is sub-rotate, the tube shorter than the sepals. In contrast to the "Blue Boy," or any known Saintpaulia, the two uppermost lobes of the corolla of this new variety are essentially equal in size and shape to the lower three lobes. There is no distinction in the new variety between the upper and lower lips. A completely outstanding feature is the presence of at least four, and usually five exserted bright yellow stamens. Another feature of the new variety is the outstanding size of the bloom, which averages between 1½ and 1¾ inches, occasionally achieving 1⅞ and even two inches.

The following is a detailed description of the new variety:

*Parentage*

Origin: Sport.
Parent variety: "Blue Boy" (unpatented).
Classification, botanic: *Saintpaulia ionantha* grandiflora (Hort.).

*Flower*

Blooming habit: Recurrent
Bud:
- *Size.*—$\frac{3}{16}$ to ⅜ inches in diameter and lengths.
- *Form.*—Quinquelobate.
- *Color.*—Dull deep purple.
- *Sepals.*—Five.
- *Shape.*—Bell-shaped.
- *Calyx.*—Size $\frac{3}{16}$ to $\frac{5}{16}$ inches—5 lobed.

Bloom:
- *Color.*—Purple.
- *Size.*—1⅜ to 1⅞ inches in diameter.
- *Form.*—Corolla subrotate, quinquelobate. All lobes essentially equal in size and shape. Lobes oval with fluted tips.
- *Borne.*—Cymose inflorescence.
- *Stems.*—Slender, reddish purple ¾ to 1½ pedicels joined to 2 inch to 3 inch stalk of cyme. 2 to 5 buds to stalk.
- *Discoloration.*—None.
- *Textures.*—Silky.
- *Fragrance.*—None.
- *Lasting quality of bloom.*—One week to ten days.

Genital organs:
- *Stamens.*—Length $\frac{5}{16}$ to ⅜ inches; number 4 to 5—usually 5.
- *Arrangement.*—Symmetrical and attached by filament to Corolla tube.
- *Color of Anther.*—Yellow.
- *Pollen.*—Color, yellow.
- *Style.*—Number, 1; length, $\frac{5}{16}$ inch; color, purple.
- *Stigma.*—Insignificant.
- *Ovaries.*—Normal.

Fruit:
- *Shape.*—Long oval—length ½ to ¾ inch, diameter $\frac{3}{16}$ to ¼ inch.
- *Color at maturity.*—Green.

*Plant*

Form: Sub-acaulescent; height 6 inches.

*Foliage.*—Quantity—12 to 24 in rosette. Color—Green. Size of leaf—1½ by 2 inches. Shape—isodiametric, ovate. Texture—upper surface: hirsute; lower surface: pubescent. Petiole—mature petiole, sturdy, oval at base; $\frac{3}{16}$ to ¼ inch in diameter at basal end, rounder at leaf end; ⅓ to $\frac{3}{16}$ inches in diameter at leaf end. Moderately hirsute purple red when immature, fading to pale green with slight purplish overtones in maturity.

The color designations according to the Munsell Book of Color, published by the Munsell Color Company, Baltimore, Maryland, in 1929, are as follows:

| | Hue | Value | Chroma | Symbol |
|---|---|---|---|---|
| Main Flower Color | Purple | 3/ | /8 | P3/8 |
| Style | do | 3/ | /10 | P3/10 |
| Anther | Yellow | 8/ | /10 | Y8/10 |
| Filaments | do | 8/ | /6 | Y8/6 |
| Pedicels | Red | 3/ | /4 | R3/4 |
| Main body of leaf | Green-yellow | 4/ | /4 | GR4/4 |
| Back of leaf | do | 8/ | /2 | GR8/2 |
| Peduncles | Red | 3/ | /4 | R3/4 |

The new variety of Saintpaulia is easily distinguishable from other varieties by the symmetrical star shape of the flowers, with scarcely distinguishable lobes; usually five stamens, but occasionally four, in contrast to the standard two showing in other varieties, and the size, averaging from 1¼ to 1¾ inches.

I claim:

A new variety of Saintpaulia plant substantially as shown and described, distinctively characterized by the symmetrical star shaped deep blue flowers having evenly sized petals, and the large average size thereof.

FRODE RAHBEK.

No references cited.